US011203000B2

(12) United States Patent
Kuan (10) Patent No.: US 11,203,000 B2
(45) Date of Patent: Dec. 21, 2021

(54) MIXING ELEMENT FOR CONTAINER ASSEMBLIES (71) Applicant: Becton, Dickinson and Company, Franklin Lakes, NJ (US)

(72) Inventor: Chee Mun Kuan, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 334 days.

(21) Appl. No.: 14/350,969

(22) PCT Filed: Oct. 18, 2012

(86) PCT No.: PCT/US2012/060771
§ 371 (c)(1),
(2) Date: Apr. 10, 2014

(87) PCT Pub. No.: WO2013/059425
PCT Pub. Date: Apr. 25, 2013

(65) Prior Publication Data
US 2014/0269160 A1 Sep. 18, 2014

Related U.S. Application Data (60) Provisional application No. 61/549,475, filed on Oct. 20, 2011.

(51) Int. Cl.
*B01F 9/10* (2006.01)
*A61M 5/20* (2006.01)
(Continued)

(52) U.S. Cl.
CPC .......... *B01F 9/103* (2013.01); *A61B 5/15003* (2013.01); *A61B 5/154* (2013.01);
(Continued)

(58) Field of Classification Search
CPC ............ A61M 5/2448; A61M 5/31596; A61M 5/284; A61M 5/2066; A61B 5/150351;
(Continued)

(56) References Cited

U.S. PATENT DOCUMENTS 3,144,966 A * 8/1964 Cook .................. B01F 7/00208
156/500
3,946,732 A * 3/1976 Hurscham ............. A61J 1/2093
604/88

(Continued)

FOREIGN PATENT DOCUMENTS

| CN | 101980770 A | 2/2011 |
|---|---|---|
| DE | 3901552 A1 | 8/1990 |

(Continued)

*Primary Examiner* — Elizabeth Insler
(74) *Attorney, Agent, or Firm* — The Webb Law Firm (57) ABSTRACT A container assembly with improved mixing dynamics for mixing substances in preparation for injection by an injection device or for the dispersion of additives in the collection and analysis of biological samples is disclosed. In one configuration, the container assembly includes a first mixing element protruding into an interior of a container. With the container rotated about its longitudinal axis, the first mixing element forms at least one vortex which effectuates mixing of a first substance provided within the container interior and a second substance provided within the container interior.

3 Claims, 12 Drawing Sheets

(51) Int. Cl.

| | | |
|---|---|---|
| *A61M 5/24* | (2006.01) | |
| *A61M 5/315* | (2006.01) | |
| *A61M 5/28* | (2006.01) | |
| *A61M 5/19* | (2006.01) | |
| *A61B 5/154* | (2006.01) | |
| *A61M 5/31* | (2006.01) | |
| *A61B 5/15* | (2006.01) | |
| *B01F 15/00* | (2006.01) | |
| *B01L 3/00* | (2006.01) | |
| *B01F 9/00* | (2006.01) | |
| *A61J 1/06* | (2006.01) | |

(52) U.S. Cl.
CPC .. *A61B 5/150351* (2013.01); *A61B 5/150755* (2013.01); *A61M 5/19* (2013.01); *A61M 5/2066* (2013.01); *A61M 5/2448* (2013.01); *A61M 5/284* (2013.01); *A61M 5/3129* (2013.01); *A61M 5/31596* (2013.01); *B01F 9/0016* (2013.01); *B01F 15/00883* (2013.01); *B01F 15/00896* (2013.01); *B01L 3/5021* (2013.01); *A61J 1/062* (2013.01); *B01L 2300/044* (2013.01); *B01L 2300/046* (2013.01)

(58) Field of Classification Search
CPC ............ A61B 5/150755; A47J 43/0722; B01F 2009/0092; B01F 2009/0094; B01F 9/103; B01L 3/5021; B01L 3/50825; B01L 2400/086; B01L 2300/08; B01L 2300/0851
See application file for complete search history.

(56) References Cited

U.S. PATENT DOCUMENTS

| 5,125,908 | A | * | 6/1992 | Cohen | A61J 1/2096 |
| | | | | | 604/110 |
| 5,139,490 | A | | 8/1992 | Vetter et al. | |
| 5,246,670 | A | | 9/1993 | Haber et al. | |
| 5,328,462 | A | | 7/1994 | Fischer | |
| 5,415,648 | A | * | 5/1995 | Malay | A61M 5/322 |
| | | | | | 604/110 |
| 5,549,574 | A | * | 8/1996 | Townsend | A61M 5/31596 |
| | | | | | 206/219 |
| 6,033,377 | A | | 3/2000 | Rasmussen et al. | |
| 6,146,361 | A | | 11/2000 | DiBiasi et al. | |
| 6,821,789 | B2 | | 11/2004 | Augello et al. | |
| 7,101,354 | B2 | * | 9/2006 | Thorne, Jr. | A61M 5/31596 |
| | | | | | 604/191 |
| 7,278,779 | B2 | * | 10/2007 | Beesley | A47J 43/06 |
| | | | | | 366/192 |
| 7,309,468 | B2 | | 12/2007 | Stevens et al. | |
| 7,503,907 | B1 | * | 3/2009 | Lesch, Jr. | A61M 5/284 |
| | | | | | 604/232 |
| 8,096,971 | B2 | * | 1/2012 | Bassarab | F26B 5/06 |
| | | | | | 604/84 |
| 2003/0163084 | A1 | | 8/2003 | Griffiths et al. | |
| 2011/0026357 | A1 | | 2/2011 | Ohtsuka et al. | |
| 2012/0209171 | A1 | * | 8/2012 | Vedrine | A61M 5/284 |
| | | | | | 604/87 |

FOREIGN PATENT DOCUMENTS

| EP | 0745369 | A2 | | 12/1996 | |
| EP | 1844804 | A1 | | 10/2007 | |
| JP | 0381558 | U | | 8/1991 | |
| JP | 06002226 | U | | 1/1994 | |
| JP | 664719 | U | | 9/1994 | |
| JP | 10504979 | A | | 5/1998 | |
| JP | 2004345958 | A | | 12/2004 | |
| JP | 200655452 | A | | 3/2006 | |
| JP | 2008539838 | A | | 11/2008 | |
| JP | 2009249012 | A | | 10/2009 | |
| JP | 2010085125 | A | | 4/2010 | |
| JP | 2016158096 | A | | 9/2016 | |
| JP | 2016187733 | A | | 11/2016 | |
| WO | 2006117340 | A1 | | 11/2006 | |
| WO | WO-2009043000 | A1 | * | 4/2009 | ............ A61M 5/284 |
| WO | 2010034462 | A1 | | 4/2010 | |
| WO | 2011026559 | A1 | | 3/2011 | |

* cited by examiner

MIXING ELEMENT FOR CONTAINER ASSEMBLIES

CROSS-REFERENCE TO RELATED APPLICATIONS

This application is the United States national phase of International Application No. PCT/US2012/060771 filed Oct. 18, 2012, and claims priority to U.S. Provisional Patent Application No. 61/549,475 filed Oct. 20, 2011, the disclosures of which are hereby incorporated in their entirety by reference.

BACKGROUND OF THE INVENTION

1. Field of the Disclosure

The present disclosure relates generally to container assemblies. More particularly, the present disclosure relates to a container assembly with improved mixing dynamics for mixing substances in preparation for injection by an injection device or for the dispersion of additives in the collection and analysis of biological samples.

2. Description of the Related Art

Injection devices such as syringes and pen needle assemblies are particularly well-suited to administer medicament which is mixed into a solution inside the cartridge or vial of the associated pen injector, such as by re-constitution or mixing of two or more components (wet or dry), such as liquid and solid powder of particles, and/or medicament having particles in the formulation suspension. In either case, poor mixing of the medicament prior to injection can lead to particles or particle agglomerations (for solid components) which may partially or wholly clog the lumen of an administering needle or uneven/unpredictable dosage (for both solid and liquid components).

Figure 1:
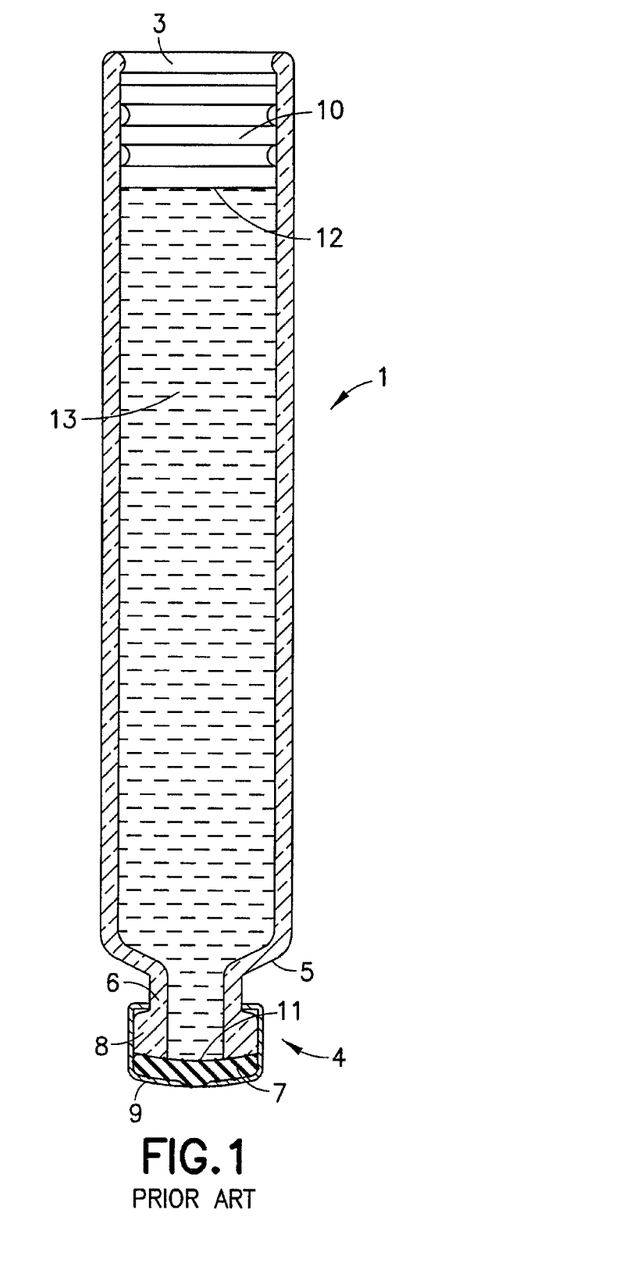
FIG. 1 is a cross-sectional view of a prior art cartridge assembly.

A typical cartridge assembly for use on a medication delivery pen as described in U.S. Pat. No. 6,146,361 is identified generally by the numeral 1 in FIG. 1 and includes an open proximal end 3 and a distal end 4 defined by an inwardly converging shoulder 5. A small diameter neck 6 projects distally from shoulder 5 on cartridge assembly 1, and is provided with a large diameter annular bead 8 extending circumferentially thereabout at the extreme distal end of neck 6. A pierceable and resealable rubber septum 7 extends completely across the open distal end defined by neck 6. Rubber septum 7 is held in place by a metallic sleeve 9 which is crimped around bead 8 at the distal end of neck 6. Medication such as insulin or heparin is pre-filled into cartridge assembly 1 and is retained therein by a rubber stopper 10. Stopper 10 is in sliding fluid-tight engagement with the tubular wall of cartridge assembly 1. Both septum 7 and stopper 10 have flat internal surfaces 11, 12 in the top and bottom of the medicament reservoir 13 of cartridge assembly 1. Distally directed forces on stopper 10 urge the medication from the medication delivery pen.

Biological sample collection containers such as vials, blood collection tubes, and syringes typically contain at least one additive to treat the collected sample which needs to be dispersed into the collected sample as completely and quickly as possible. One example of such an additive is an anticoagulant such as heparin; poor mixing of heparin with blood samples leads to the formation of microclots in blood samples.

Figure 2:
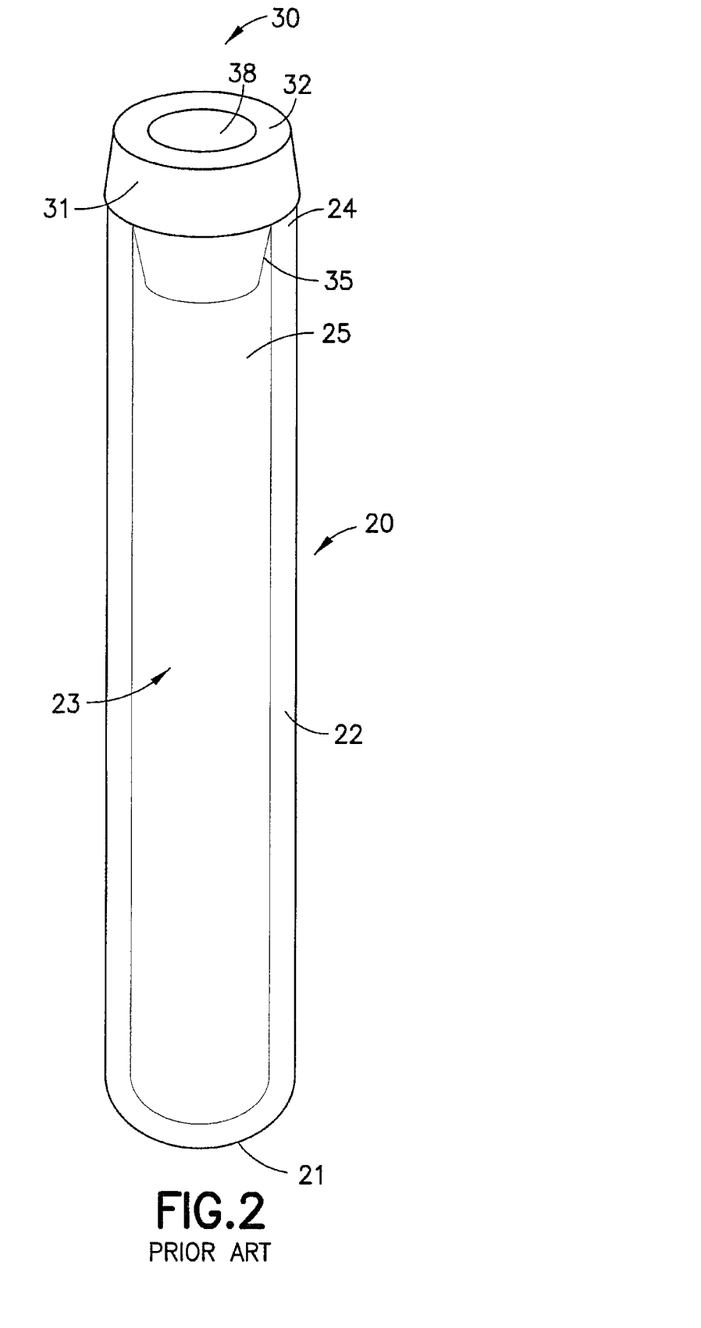
FIG. 2 is a perspective view of a prior art evacuated blood collection tube and a closure located at a top portion of the blood collection tube.
Figure 3:
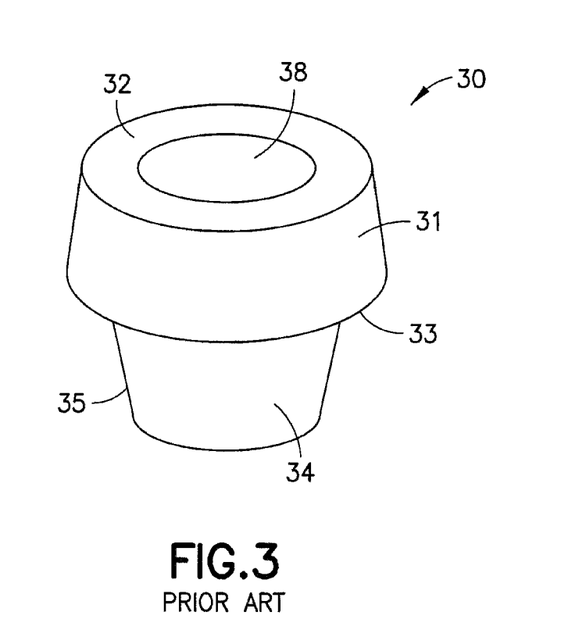
FIG. 3 is a perspective view of the closure of FIG. 2.
Figure 4:
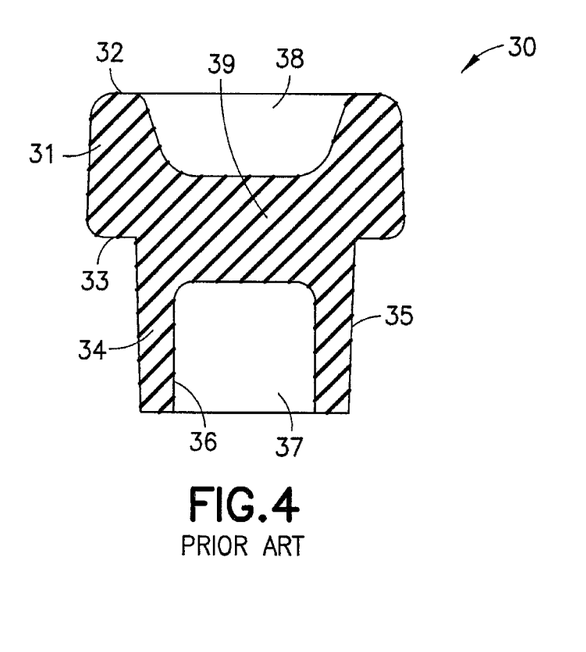
FIG. 4 is a cross-sectional view taken along line 4-4 of FIG. 3.

FIGS. 2-4 illustrate an example of a blood collection tube having a single open end and closure. FIG. 2 illustrates the tube 20 and closure 30 ready for drawing a blood sample into enclosed evacuated interior fluid reservoir 23. Tube 20 has bottom wall portion 21 and sidewall portion 22 continuous therewith. Sidewall portion 22 has a top edge 24 and defines an open end 25. A straight sidewall portion is shown for the tube 20, but complex sidewall shapes, for other containers, are also possible. FIGS. 2-4 show a closure 30 for open end 25. Closure 30 may be one of a variety of forms including, but not limited to, rubber closures, metallic seals, metal-banded rubber seals, and seals of different polymers and designs. Closure 30 includes an annular upper portion 31 having a top wall 32. Upper portion 31 has a lower wall or lip 33, which extends over top edge 24 of tube 20 when the closure is in the tube. Closure 30 also includes a lower annular portion or skirt 34 having an outside wall 35 which forms an interference fit with the inside wall surface of tube 20 to maintain the closure in the tube. Skirt 34 also has an inside wall surface 36, which defines a well 37. Top wall 32 defines a cavity 38. A septum 39 separates well 37 and cavity 38 for penetration by a cannula when the tube assembly is ready for use.

Thus medicament and sample collection containers are typically cylindrical vessels having flat or recessed internal surfaces on the top and bottom of the internal chamber and as such have poor content mixing characteristics. Thus little turbulence is created to mix the contents when these vessels are inverted end-over-end or rolled, especially in instances where there is no headspace in the vessel or if the components are similar in density.

Some manufacturers such as Radiometer include a small mixing ball in insulin pen cartridges as part of the safePICO Mixer system, however the ball may interfere with the full expression of pen cartridge contents and change the established clinical practice. The dead space within the cartridge may also be larger, leading to increased wastage.

What is needed therefore are medicament and sample collection containers with improved mixing dynamics in order to mix the contents when these vessels are inverted end-over-end or rolled, especially in instances where there is no headspace in the vessel or if the components are similar in density.

SUMMARY OF THE INVENTION

The present disclosure provides a container assembly with improved mixing dynamics for mixing substances in preparation for injection by an injection device or for the dispersion of additives in the collection and analysis of biological samples. In one configuration, the container assembly includes a first mixing element protruding into an interior of a container. With the container rotated about its longitudinal axis, the first mixing element forms at least one vortex which effectuates mixing of a first substance and a second substance contained within the container assembly.

In accordance with an embodiment of the present invention, a container assembly for containing a first substance and a second substance includes a container having a first end, a second end, and a sidewall extending therebetween and defining a container interior, the container defining a container longitudinal axis. The container assembly includes a first closure sealing the first end of the container and a second closure sealing the second end of the container. The container assembly further includes a first mixing element protruding into the container interior, whereby, with the container rotated about the container longitudinal axis, the first mixing element forms at least one vortex which effectuates mixing of a first substance provided within the container interior and a second substance provided within the container interior.

In one configuration, the first mixing element is located on a portion of the first closure. In another configuration, the first mixing element is located on a portion of the second closure. In yet another configuration, the first mixing element is located on an internal surface of the sidewall of the container. In one configuration, the first mixing element forms an asymmetric mixing pattern within the substance provided within the container interior. In another configuration, the container assembly further includes a second mixing element protruding into the container interior, whereby, with the container rotated about the container longitudinal axis, the first mixing element and the second mixing element form the at least one vortex which effectuates mixing of the first substance and the second substance within the container assembly. In yet another configuration, the first mixing element includes at least one mixing fin. In such a configuration, the at least one mixing fin includes a top portion, a bottom portion, a first mixing face extending from the bottom portion to the top portion at a first angle, and a second mixing face extending from the bottom portion to the top portion at a second angle. In one embodiment, the first angle equals the second angle. In another embodiment, the first angle is greater than the second angle. In yet another embodiment, the first angle is less than the second angle. In one embodiment, the first and the second mixing faces have the same shape. In another embodiment, the first mixing face has a different shape than the second mixing face. In yet another embodiment, the first mixing element includes three mixing fins equally spaced about the circumference of a portion of the first closure. In one embodiment, the first mixing element includes at least one inclined surface of a portion of the first closure.

In a further configuration, the container assembly includes a first substance within the container interior. Optionally, the container assembly includes a second substance within the container interior.

In accordance with another embodiment of the present invention, a container assembly for containing a first substance and a second substance includes a container having a first end, a second end, and a sidewall extending therebetween and defining a container interior, the container defining a container longitudinal axis. The container assembly includes a first closure sealing the first end of the container and a second closure sealing the second end of the container. The container assembly further includes a first mixing element protruding into the container interior, the first mixing element located on a portion of the first closure, and a second mixing element protruding into the container interior, the second mixing element located on a portion of the second closure, whereby, with the container rotated about the container longitudinal axis, the first mixing element and the second mixing element form at least one vortex which effectuates mixing of a first substance provided within the interior of the container and a second substance provided within the container interior.

In one configuration, the first closure includes a stopper slidably disposed within the container interior of the container, the stopper sized relative to the container to provide sealing engagement with the sidewall of the container. In a further configuration, the container assembly includes a first substance within the container interior. Optionally, the container assembly includes a second substance within the container interior.

In accordance with another embodiment of the present invention, a container assembly for containing a first substance and a second substance includes a container having a first end, a second end, and a sidewall extending therebetween and defining a container interior, the container defining a container longitudinal axis. The container assembly includes a first closure sealing the first end of the container and a second closure sealing the second end of the container. The container assembly further includes mixing means for creating a vortex upon rotation of the container about the container longitudinal axis, the vortex effectuating mixing of a first substance provided within the container interior and a second substance provided within the container interior.

Optionally, the container assembly includes a first substance within the container interior. In another configuration, the container assembly includes a second substance within the container interior.

In accordance with another embodiment of the present invention, a method of mixing a first substance and a second substance contained in a container assembly includes providing a container assembly for containing a first substance and a second substance. The container assembly includes a container having a first end, a second end, and a sidewall extending therebetween and defining a container interior. The container defines a container longitudinal axis, and includes a first closure sealing the first end of the container, and a second closure sealing the second end of the container. The container assembly includes a first mixing element protruding into the container interior. The method includes providing at least a first substance and a second substance within the container interior, and rotating the container about the container longitudinal axis. The method includes forming at least one vortex via the first mixing element during rotation, such that the at least one vortex effectuates mixing of the first substance and the second substance within the container assembly.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

According to embodiments of the present disclosure, medicament and biological sample collection containers may include tubes, bottles, vials, syringes, flasks, and single use disposable containers, for example. The present disclosure is described below with respect to a cartridge assembly of a medicament delivery pen as a medicament container and an evacuated blood collection tube as a sample container, but it will be apparent to one skilled in the art that the description is equally applicable to any other medicament or sample collection containers.

In the following discussion, "distal" refers to a location on the cartridge assembly or blood collection assembly of the present disclosure that is, during normal use, closest to a patient who is receiving treatment and farthest from a clinician administering the treatment to the patient and "proximal" refers to the opposite direction of distal, i.e., farthest from the patient who is receiving treatment and closest to the clinician administering the treatment to the patient. Furthermore, in the following discussion, "proximal direction" refers to a direction of movement away from the patient who is receiving treatment and toward the clinician administering the treatment to the patient and "distal direction" refers to a direction of movement toward the patient who is receiving treatment and away from the clinician administering the treatment to the patient. For purposes of this disclosure, the above-mentioned references are used in the description of the components of a container assembly in accordance with the present disclosure.

The embodiments of the present disclosure provide improved mixing dynamics in a container assembly by the incorporation of at least one mixing element within the interior of a container of the container assembly for mixing substances in preparation for injection by an injection device or for the dispersion of additives during the collection and analysis of biological samples.

FIGS. 5 to 18 illustrate various embodiments of mixing elements for container assemblies according to the present disclosure. The mixing elements of the present disclosure may be incorporated into the design of closures, stoppers, plungers, or similar components in syringes, cartridges, or tubes. Alternatively, the mixing elements of the present disclosure may be directly molded into a portion of the tubes, syringe assemblies, cartridge assemblies, or similar components. In some configurations, one mixing element may be present in the container assembly. In other configurations, two or more mixing elements may be present in the container assembly. For example, a mixing element may be located at one or both ends of a container assembly.

Figure 5:
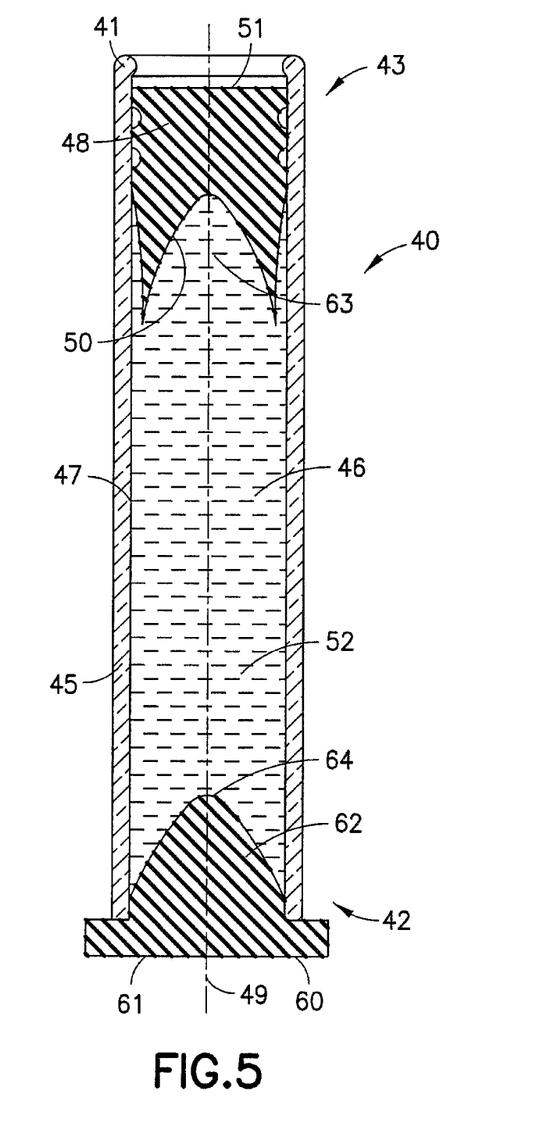
FIG. 5 is a cross-sectional view of a cartridge assembly in accordance with an embodiment of the present invention.
Figure 6:
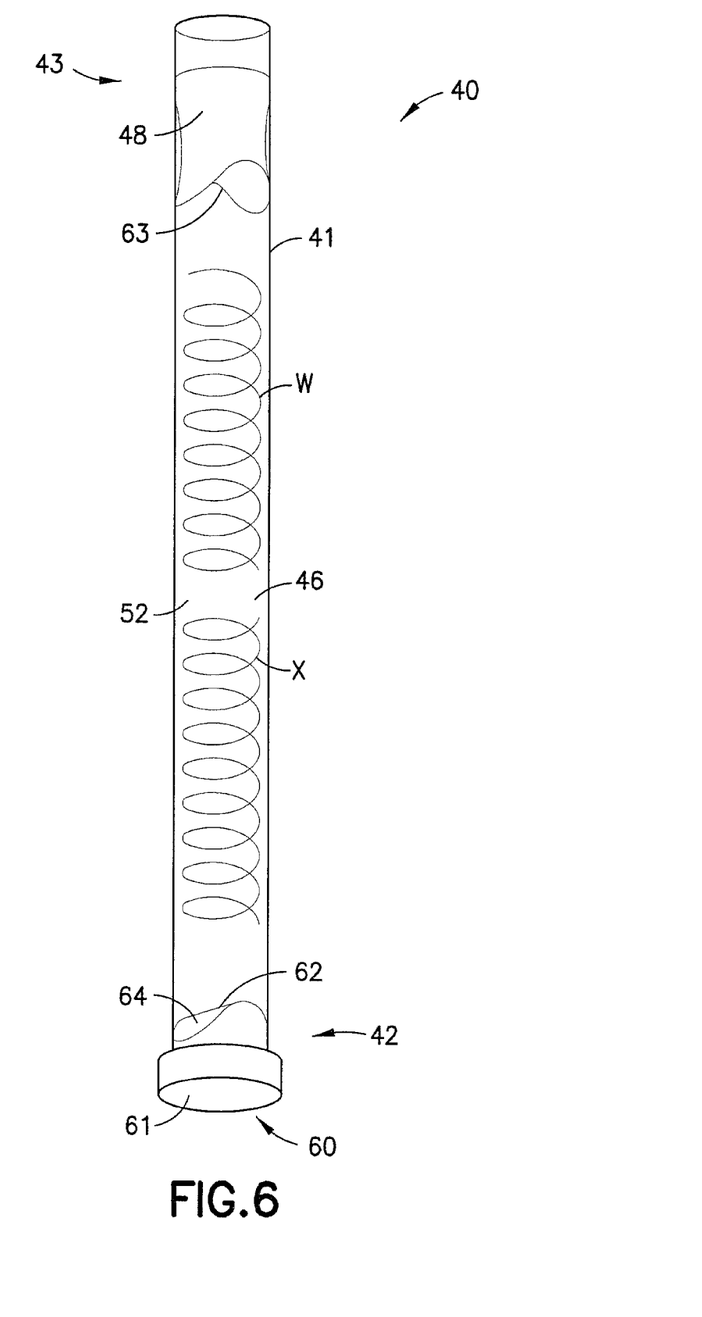
FIG. 6 is a perspective view of the cartridge assembly of FIG. 5 in accordance with an embodiment of the present invention.

Referring to FIGS. 5 and 6, a cartridge assembly or container assembly 40 includes a tube or container 41 having a distal end 42 and a proximal end 43. Container 41 defines a container longitudinal axis 49. In one embodiment, tube 41 is an elongated, hollow, cylindrically-shaped container. In other embodiments, tube 41 may include other shapes and sizes. For example, tube 41 may have other multi-sided polygon cross-sectional shapes, such as square or rectangular cross-sectional shapes.

Tube 41 of cartridge 40 includes a rigid wall or sidewall 45 that defines an internal chamber or container interior 46 extending between distal end 42 and proximal end 43. The sidewall 45 of tube 41 defines an internal surface 47 for receiving a first closure 48 which seals one of the ends of container 41.

In one embodiment, the first closure 48 may be a stopper. Referring to FIGS. 5 and 6, container assembly 40 includes stopper 48 which is slidably disposed within container interior 46, and in sealing contact with the internal surface of sidewall 45 of container 41. Stopper 48 is sized relative to container 41 to provide sealing engagement with the interior surface of sidewall 45 of container 41. Additionally, stopper 48 may include one or more annular ribs extending around the periphery of stopper 48 to increase the sealing engagement between stopper 48 and the interior surface of sidewall 45 of container 41. In alternate embodiments, a singular O-ring or a plurality of O-rings may be circumferentially disposed about stopper 48 to increase the sealing engagement with the interior surface of sidewall 45.

Referring to FIGS. 5 and 6, in one embodiment, stopper 48 is slidably positioned in fluid tight engagement with internal surface 47, and is able to slide distally and proximally along longitudinal axis 49. Stopper 48 includes a distal face 50 and a proximal face 51. The diameter of stopper 48 is approximately equal to or only slightly greater or smaller than the internal diameter of tube 41. Stopper 48 is in slidable contact with internal surface 47 of tube 41 and provides a fluid-tight seal so that a medicament fluid can be held within a fluid reservoir 52 formed within chamber 46 between distal end 42 of tube 41 and distal face 50 of stopper 48, thereby preventing the sample from leaking from the proximal end 43 tube 41.

Distal end 42 of tube 41 is sealed by a closure 60 to form a liquid impermeable seal to contain the blood sample. The closure 60 includes an external end 61 and an internal end 62 structured to be at least partially received within the tube 41. Portions of the closure 60 adjacent the open distal end 42 of the tube 41 define a maximum outer diameter which exceeds the inside diameter of the tube 41. The inherent resiliency of closure 60 can ensure a sealing engagement with the internal surface 47 of the wall 45 of the tube 41. Portions of the closure 60 extending downwardly from the internal end 62 may taper from a minor diameter which is approximately equal to, or slightly less than, the inside diameter of the tube 41 to a major diameter that is greater than the inside diameter of the tube 41 adjacent the distal end 42. Thus, the internal end 62 of the closure 60 may be urged into a portion of the tube 41 adjacent the distal open end 42. Closure 60 is such that it can be pierced by a needle or other cannula to allow medicament to flow out of or into the tube 41 as is known in the art. Preferably, closure 60 is resealable. Suitable materials for closure 60 include, for example, elastomers such as silicone rubber, natural rubber, styrene butadiene rubber, ethylene-propylene copolymers and polychloroprene, and thermoplastic elastomers.

A cavity 63 in the distal face 50 of stopper 48 and a mixing fin 64 extending from the internal end 62 of closure 60 provide a mixing element at each end of the fluid reservoir 52. When the cartridge 40 is rolled by rotating the cartridge about longitudinal axis 49, the cavity 63 and mixing fin 64 create vortices (w, x) that promote thorough mixing of the contents of the fluid reservoir 52 as shown in FIG. 6. This is particularly useful in instances where there is no air (headspace) in the fluid reservoir of a collection vessel. Tipping such devices end-over-end does little to mix the contents, especially if the components are similar in density. Vessels with a cylindrical internal fluid reservoir such as vials, insulin pen cartridges, and syringes typically have flat internal surfaces in the top and bottom of the fluid reservoir. Therefore little turbulence is created when these vessels are rolled.

Container 41 or a similar biological sample collection container according to embodiments of the present disclosure may be made of one or more than one of the following representative materials: polypropylene, polyethylene, polyethyleneterephthalate (PET), polystyrene, polycarbonate, cellulosics, glass products, or combinations thereof. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF, and perfluoroalkoxy resins. One exemplary glass product is PYREX® (available from Corning Glass, Corning, N.Y.).

FIGS. 7 to 16 illustrate various embodiments of mixing elements. Each mixing element embodiment can be used in a closure, stopper, or plunger at one end of the fluid reservoir or as one of a possible pair of matching or complimentary mixing elements at each end of the fluid reservoir. The pair of mixing elements in FIGS. 5 and 6 (cavity 63 in the distal face 50 of stopper 48 and mixing fin 64 extending from the internal end 62 of closure 60) is an embodiment of a pair of complimentary mixing elements.

Figure 7:
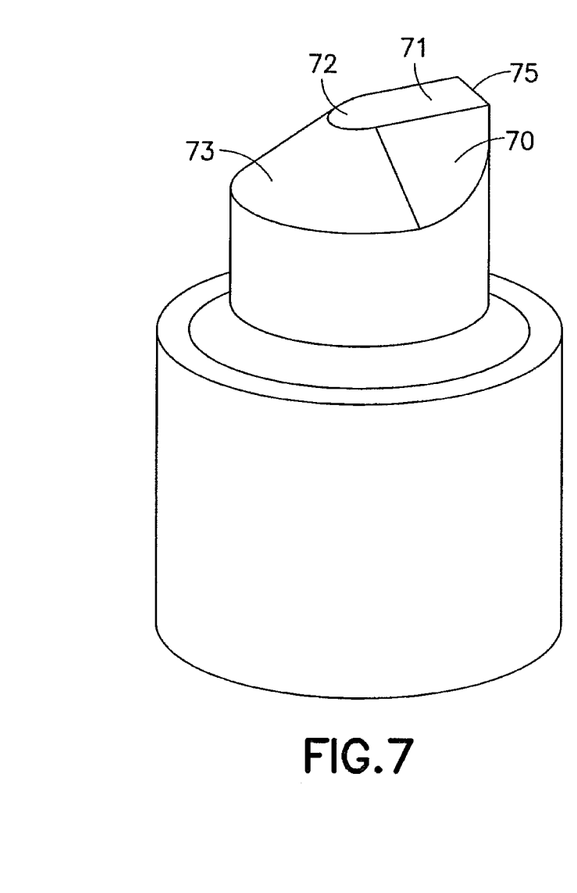
FIG. 7 is a perspective view of a mixing element in accordance with an embodiment of the present invention.
Figure 8:
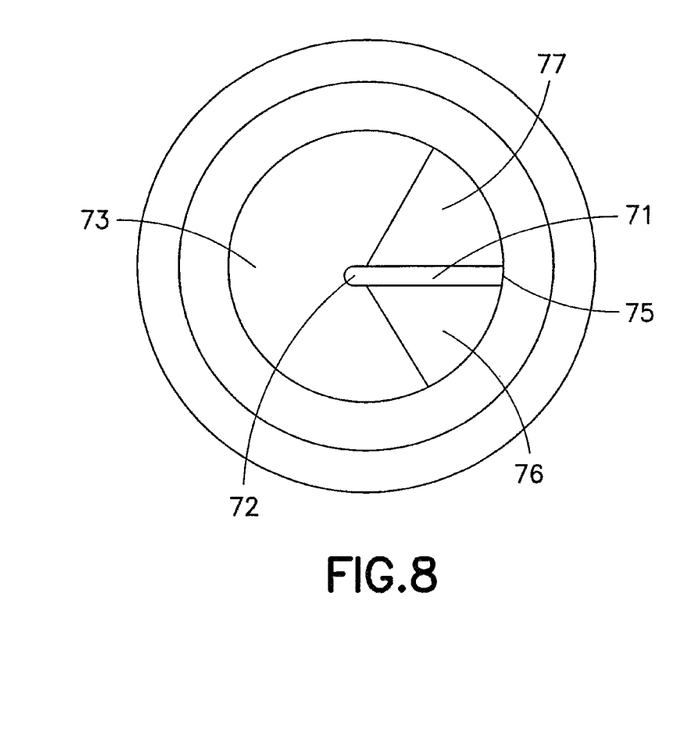
FIG. 8 is a plan view of the mixing element of FIG. 7 in accordance with an embodiment of the present invention.
Figure 9:
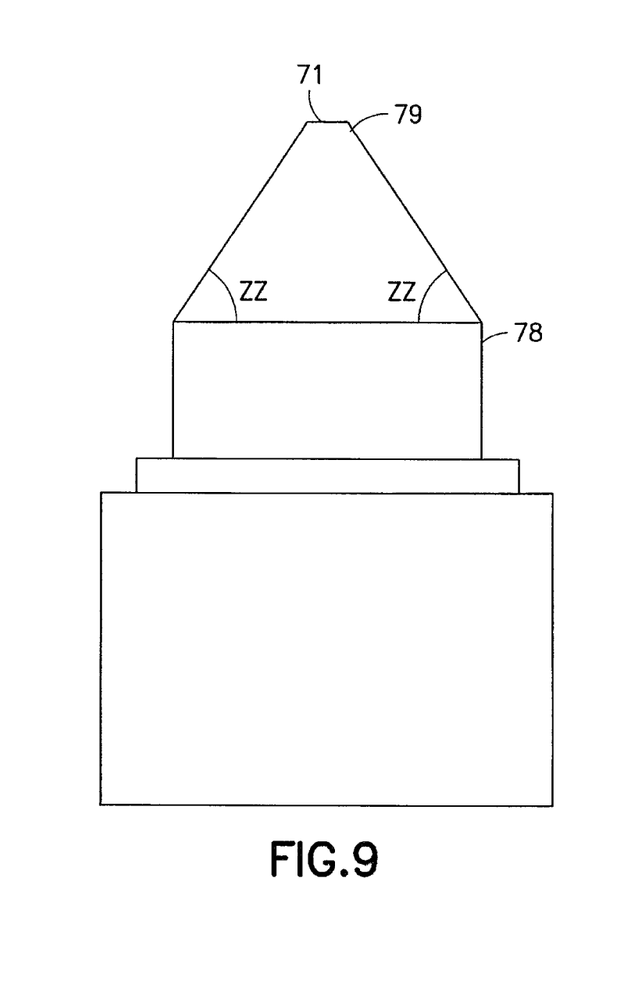
FIG. 9 is a side elevation view of the mixing element of FIG. 7 in accordance with an embodiment of the present invention.

Referring to FIGS. 7-9, a single mixing fin 70 includes an upper land section 71 extending from a center 72 of a cone 73 to a point on an outer circumference 75 of closure 60. Mixing fin 70 has a first mixing face 76 and a second mixing face 77 which extend from a bottom portion 78 to a top portion 79 at an angle of approximately 60 degrees, although angle ZZ can be an angle in the range of 0 to 90 degrees.

Figure 10:
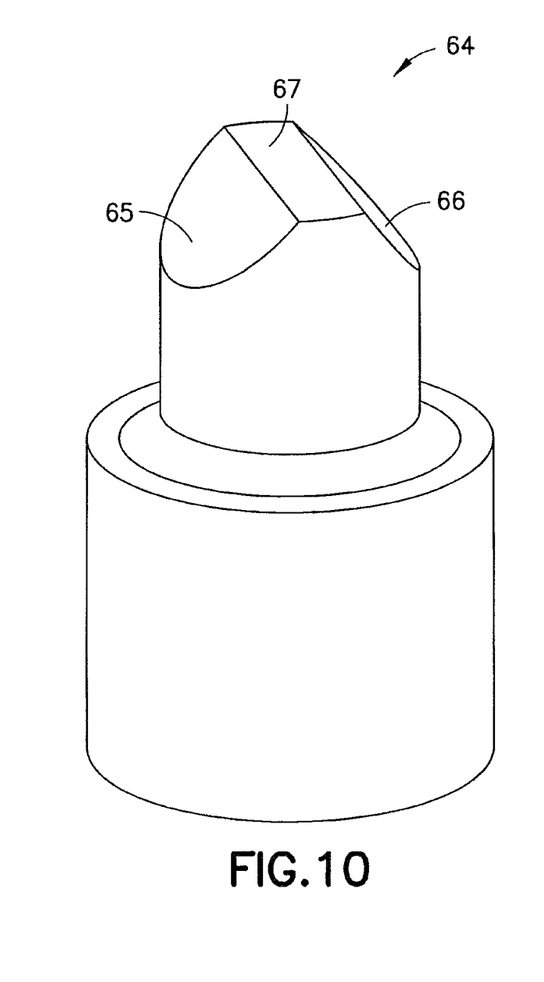
FIG. 10 is a perspective view of a mixing element in accordance with another embodiment of the present invention.

Referring to FIGS. 5, 6, and 10, first and second mixing fins are set 180 degrees apart around the circumference such that they extend across the entire diameter of, for example, an internal surface of a first or second closure. The first mixing face 65, a second mixing face 66, and an upper land section 67 of the first and second mixing fins are aligned together to form a unitary mixing fin 64.

Figure 11:
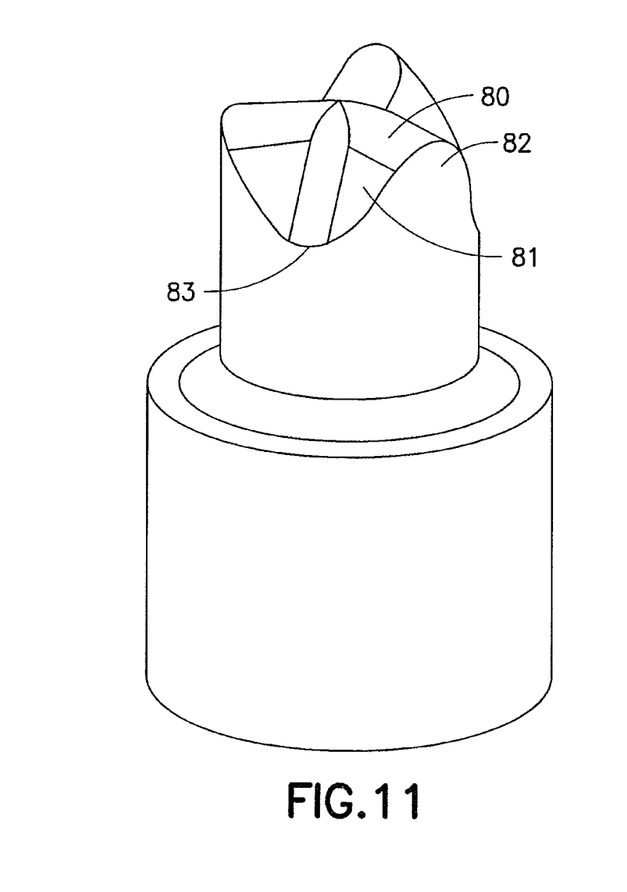
FIG. 11 is a perspective view of a mixing element in accordance with another embodiment of the present invention.
Figure 12:
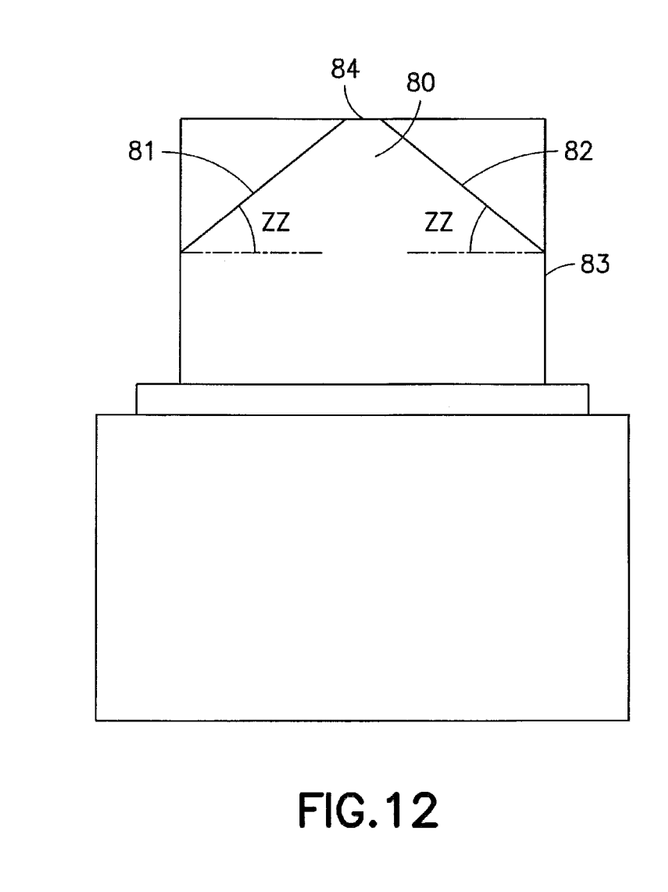
FIG. 12 is a side elevation view of the mixing element of FIG. 11 in accordance with an embodiment of the present invention.
Figure 13:
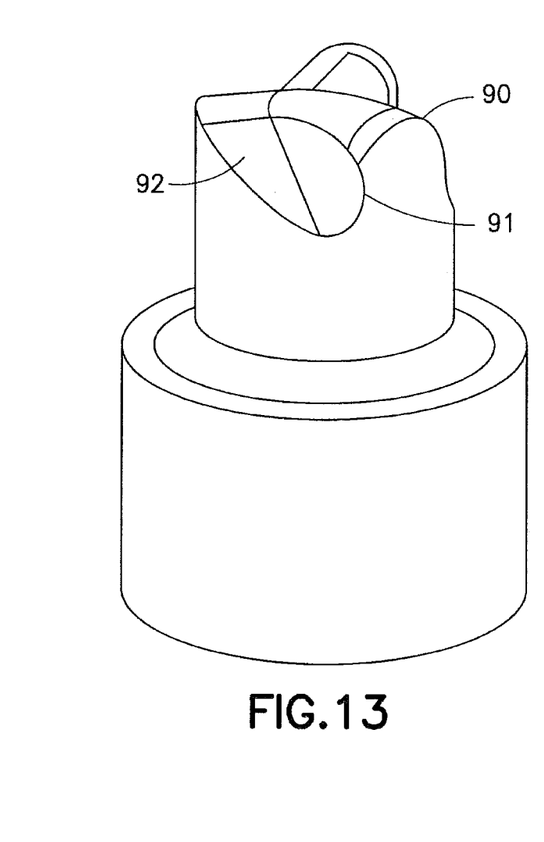
FIG. 13 is a perspective view of a mixing element in accordance with another embodiment of the present invention.
Figure 14:
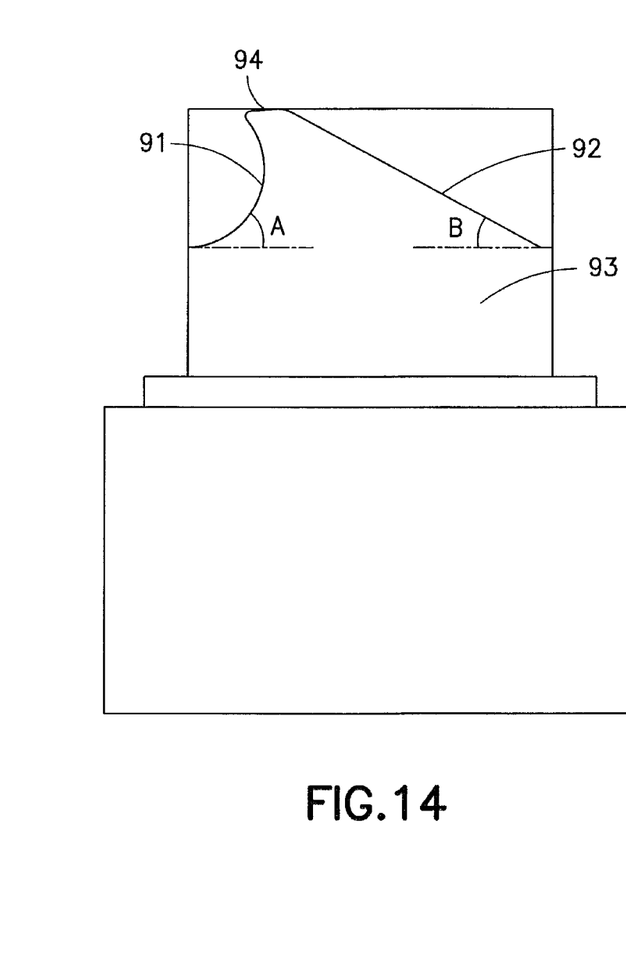
FIG. 14 is a side elevation view of the mixing element of FIG. 13 in accordance with an embodiment of the present invention.

Referring to FIGS. 11-14, first, second, and third mixing fins are separated equally (120 degrees) around the circumference of the inner surface of, for example, a first or second closure. FIG. 12 illustrates an embodiment in which a mixing fin 80 has a first mixing face 81, and a second mixing face 82 extending from a bottom portion 83 to a top portion 84 at the same angle ZZ which, in this particular embodiment, is 45 degrees (however the angle ZZ can be in the range of 5 to 90 degrees). FIG. 14 illustrates an embodiment in which the angle A that a first mixing face 91 for a mixing fin 90, extends from a bottom portion 93 to a top portion 94 differs from angle B that a second mixing face 92 extends from bottom portion 93 to top portion 94. Each angle A and B can be in the range of 5 to 90 degrees. Furthermore, first mixing face 91 has a different shape/profile than that of second mixing face 92. This difference in mixing face attributes can be defined as an asymmetrical mixing fin.

Asymmetrical mixing fins (as shown in FIG. 14, where one mixing face has a different incline angle and/or shape from the second mixing face) are preferred to mixing fins that are symmetrical but are otherwise similar (as shown in FIG. 10). Asymmetry in a mixing element results in a net residual current moving in one direction within the fluid reservoir every time the vessel is rolled back and forth. The mixing face of the element that is more vertical has more resistance, so it always exerts more force on the fluid contents of the container than the other mixing face. Symmetrical mixing element designs having similar shaped and angled mixing faces exert equal force in both directions, which may then cancel each other out when the device is rolled back & forth.

Figure 15:
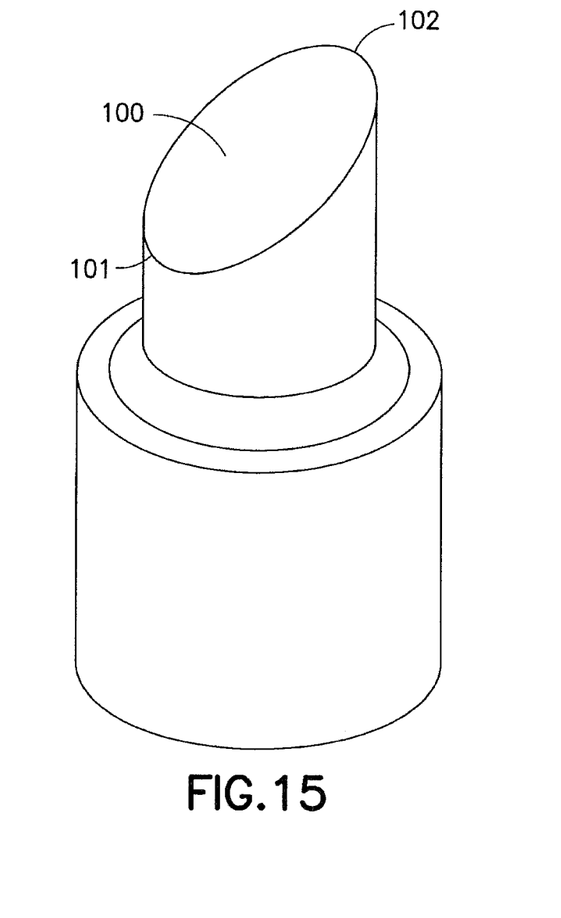
FIG. 15 is a perspective view of a mixing element in accordance with another embodiment of the present invention.
Figure 16:
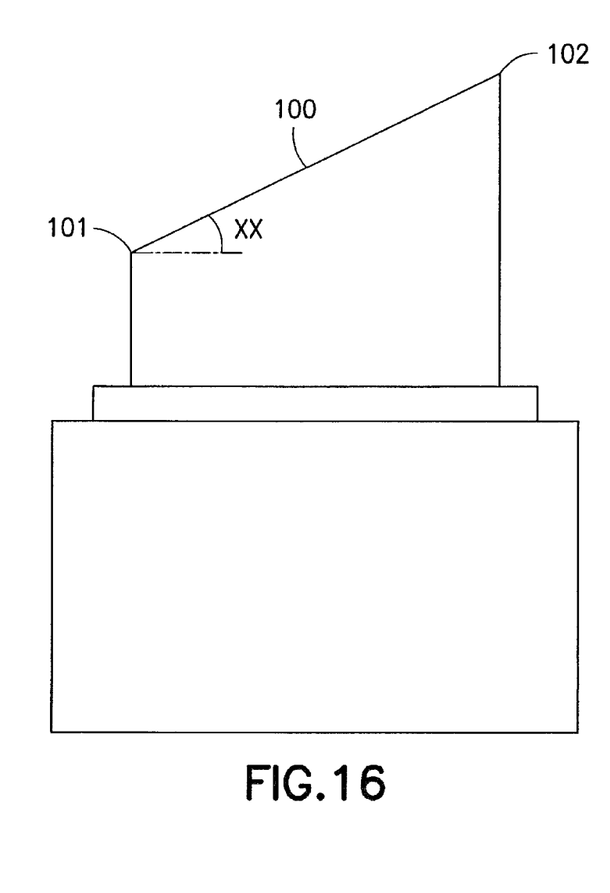
FIG. 16 is a side elevation view of the mixing element of FIG. 15 in accordance with an embodiment of the present invention.

Referring to FIGS. 15 and 16, a mixing element is illustrated using an inclined face 100 of the internal surface of a closure which extends from a low point 101 on the outer circumference to a high point 102 on the outer circumference across the diameter of the internal surface at an angle XX (which is in the range of 5 to 90 degrees) to form a truncated cylinder shape.

Figure 17:
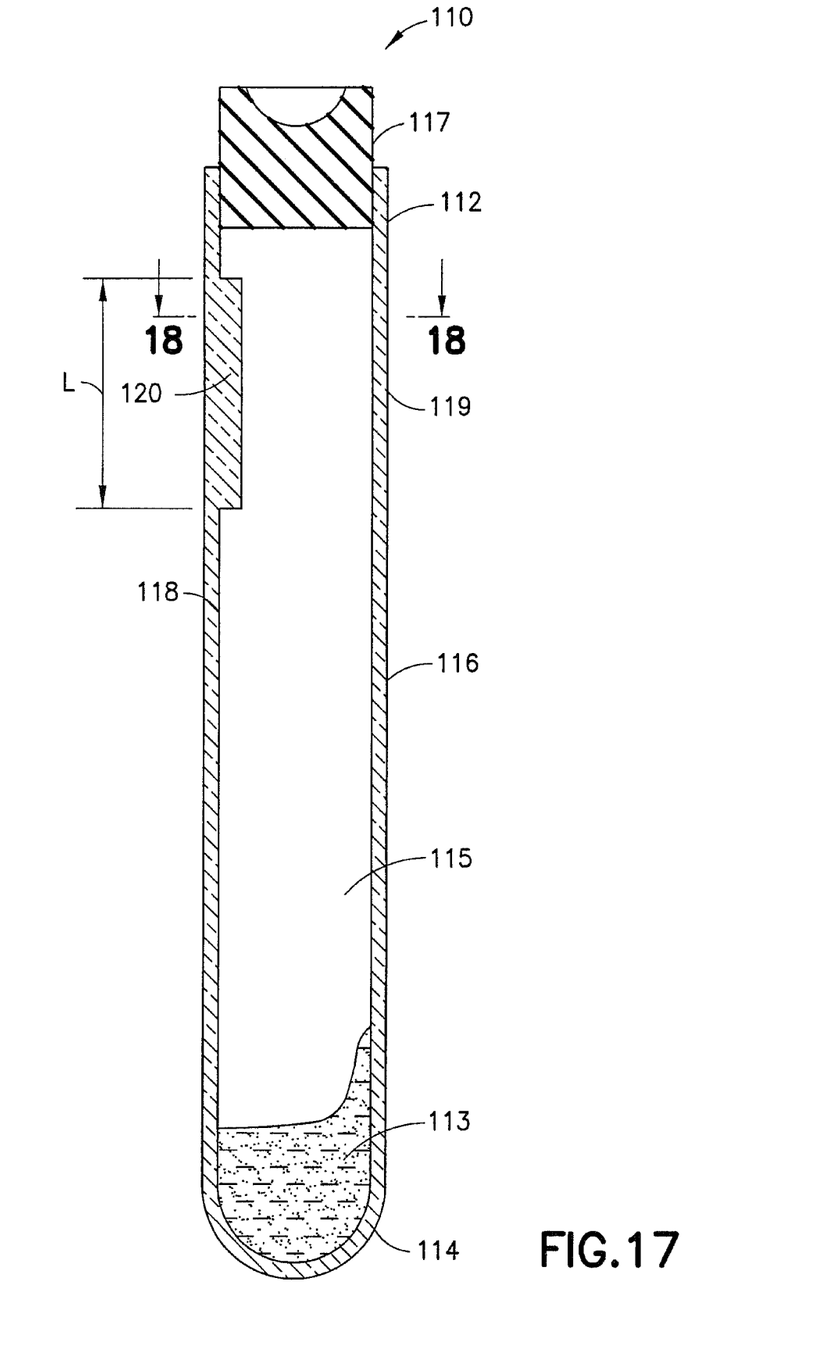
FIG. 17 is a cross-sectional view of a blood collection tube in accordance with an embodiment of the present invention.
Figure 18:
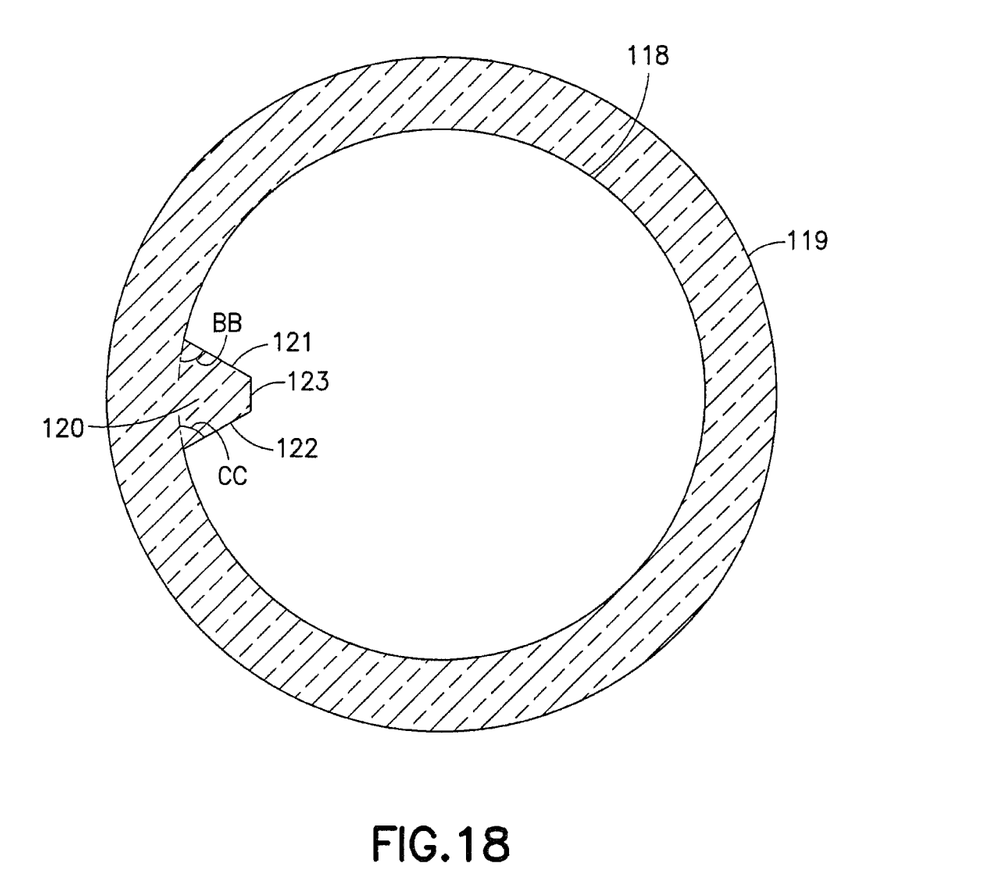
FIG. 18 is a cross-sectional view taken along line 18-18 of FIG. 17.

FIGS. 17 and 18 illustrate an embodiment in which a mixing element is directly molded into the end of a blood collection tube 110. The tube 110 contains an open upper end 112, a lower closed end 114, and sidewalls 116 having an inner wall 118 and an outer wall 119. A separating gel 113 is located within the container, at or adjacent the closed end 114.

The tube 110 is provided with a pierceable closure 117, which seals open upper end 112 that may be pierced by the non-patient end of a double ended blood collection needle. Suitable materials for closure 117 include, for example, elastomers such as silicone rubber, natural rubber, styrene butadiene rubber, ethylene-propylene copolymers and polychloroprene, and thermoplastic elastomers. The tube 110 is generally evacuated to pressure which is less than atmospheric pressure, such that upon piercing by such a needle, blood is drawn into the tube. Details of evacuated blood collection tubes and blood collection are well known to those skilled in the art.

A single mixing fin 120 is located towards open upper end 112 which projects from inner wall 118 into a fluid reservoir 115 to allow for the incorporation of an additive into the collected blood sample immediately after collection of the sample and prior to separation by centrifugation. Mixing fin 120 has a first 121 and a second 122 mixing faces which extend from inner wall 118 to a top portion 123 at angles BB and CC which in this particular embodiment are both at 60 degrees (however each angle BB and CC can be in the range of 5 to 355 degrees). The shape and angles of the two mixing faces, as well as the length of mixing fin 120, are all variables which can be adjusted to provide sufficient mixing for each particular type of sample or application.

A biological sample collection container (such as a blood collection tube) generally must go through processing steps by which various additives are disposed in the container. For example, additives useful in blood or urine analysis, e.g., procoagulants or anticoagulants, are often disposed into the tube. As is known in the art, blood analysis is often performed on serum, and procoagulants are typically used to enhance the rate of clotting. Such procoagulants include silica particles or enzyme clot activators such as elagic acid, fibrinogen, and thrombin. If plasma is desired for analysis, an anticoagulant is generally used to inhibit coagulation, such that blood cells can be separated by centrifugation. Such anticoagulants include chelators such as oxalates, citrate, and EDTA, and enzymes such as heparin. Additives are disposed in the primary containers in any suitable manner, liquid or solid, including dissolution in a solvent, or disposing in powdered, crystallized, or lyophilized form.

Additional additives can include a stabilizing agent for stabilizing or inhibiting the degradation of a component within the biological sample such as nucleic acid or proteins in a blood sample. Examples of suitable agents for stabilizing and preserving nucleic acids and/or preventing gene induction include cationic compounds, detergents, chaotropic substances, and mixtures thereof, which are described in U.S. Pat. No. 6,821,789, the entire disclosure of which is hereby incorporated by reference. A protein stabilizing agent may include at least one protease inhibitor. Suitable examples include, but are not limited to, inhibitors of proteases such as serine proteases, cysteine proteases, aspartic proteases, metalloproteases, thiol proteases, exopeptidases, and the like, which are described in U.S. Pat. No. 7,309,468, the entire disclosure of which is hereby incorporated by reference.

Example

The following example is intended to illustrate embodiments of the present disclosure and is not intended to limit the present disclosure.

Evaluation of Mixing Element Designs

Method: Identical cartridges/syringes were fitted on both ends with closures and stoppers having mixing elements of 3 different designs (labeled M Pro as shown in FIGS. 9 and 10, SE as shown in FIGS. 11 and 12, and CE as shown in FIGS. 13 and 14) according to embodiments of the present disclosure. A BD Preset syringe was also used as a control which had no mixing elements at either end of the fluid reservoir. Each syringe was filled with 2 ml water and 200 µl red dye (without mixing) such that no headspace was present and the red dye was contained in a distinct layer at the base of the fluid reservoir with a transparent layer of water located above. The syringes were then loaded onto a test rig which was held in the vertical position and spun each syringe with equal force & speed in a reciprocating motion.

Results: The cartridges/syringes having closures and stoppers fitted with mixing elements SE, CE, & M Pro were able to mix the dye into water completely after 5 seconds. The control failed to show complete mixing even after 30 seconds. These experiments were repeated several times and the results were position-independent & reproducible. The CE design appeared to give the highest degree of mixing when comparing the various mixing elements SE, CE, & M Pro.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A container assembly for mixing substances in preparation for an injection or dispersion of an additive in a biological sample, the container assembly comprising:
   a container having a first end, a second end, and a sidewall extending therebetween and defining a container interior, the container defining a container longitudinal axis, the container being configured to mix the substances in preparation for the injection or disperse the additive in the biological sample;
   a first closure comprising a single-piece stopper having a proximal end and a distal end, the distal end of the stopper sealing the first end of the container;
   a second closure sealing the second end of the container;
   a first mixing element protruding into the container interior, the first mixing element defining a cavity in a portion of the first closure, the cavity opening into the container interior; and
   a second mixing element protruding into the container interior, the second mixing element comprising a protrusion located on a portion of the second closure, the protrusion comprising a substance-contacting surface that contacts the substances in the container interior, wherein the substance-contacting surface is asymmetrical about the container longitudinal axis, and whereby, with the container rotated about the container longitudinal axis, the first mixing element forms at least one vortex and the second mixing element forms at least one vortex rotating in a direction opposite to the at least one vortex formed by the first mixing element which effectuates mixing of a first substance provided within the container interior and a second substance provided within the container interior.

2. The container assembly of claim 1, wherein the stopper is slidably disposed within the container interior of the container, the stopper sized relative to the container to provide sealing engagement with the sidewall of the container.

3. The container assembly of claim 1, wherein the first closure is entirely disposed in the container during mixing.

* * * * *